US008652814B2

(12) United States Patent
Okuyama et al.

(10) Patent No.: US 8,652,814 B2
(45) Date of Patent: Feb. 18, 2014

(54) METHOD FOR PRODUCTION OF DHA-CONTAINING PHOSPHOLIPID THROUGH MICROBIAL FERMENTATION

(75) Inventors: Hidetoshi Okuyama, Sapporo (JP); Yoshitake Orikasa, Sapporo (JP); Takanori Nishida, Sapporo (JP)

(73) Assignees: National University Corporation Hokkaido University, Hokkaido (JP); Research of Microbes Co., Ltd., Hokkaido (JP)

( * ) Notice: Subject to any disclaimer, the term of this patent is extended or adjusted under 35 U.S.C. 154(b) by 148 days.

(21) Appl. No.: 12/451,860

(22) PCT Filed: Jun. 3, 2008

(86) PCT No.: PCT/JP2008/001394

§ 371 (c)(1), (2), (4) Date: Dec. 3, 2009

(87) PCT Pub. No.: WO2008/149542

PCT Pub. Date: Dec. 11, 2008

(65) Prior Publication Data

US 2010/0105113 A1 Apr. 29, 2010

(30) Foreign Application Priority Data

Jun. 4, 2007 (JP) ................................ 2007-148398

(51) Int. Cl.
*C12P 7/64* (2006.01)

(52) U.S. Cl.
USPC ........................................................ 435/134

(58) Field of Classification Search
None
See application file for complete search history.

(56) References Cited

U.S. PATENT DOCUMENTS

| | | | | |
|---|---|---|---|---|
| 7,022,512 | B2 * | 4/2006 | Barclay | 435/254.1 |
| 7,968,737 | B2 | 6/2011 | Kawashima et al. | |
| 2004/0161831 | A1 | 8/2004 | Komazawa et al. | |
| 2007/0082384 | A1 | 4/2007 | Barclay | |

FOREIGN PATENT DOCUMENTS

| | | | |
|---|---|---|---|
| EP | 0 823 475 | A | 2/1998 |
| EP | 1 138 759 | A | 10/2001 |
| JP | S59-39258 | | 3/1984 |
| JP | H8-202405 | | 3/1996 |
| JP | H8-509355 | | 10/1996 |
| JP | H9-284 | | 1/1997 |
| JP | H10-72590 | | 3/1998 |
| JP | H10-310556 | | 11/1998 |
| JP | 2001-275656 | | 10/2001 |
| JP | 2001-309779 | | 11/2001 |
| JP | 2003-292 | | 1/2003 |
| JP | 2004-121019 | | 4/2004 |
| JP | 2004-298798 | | 10/2004 |
| JP | 2005-102680 | | 4/2005 |
| JP | 2005-530519 | | 10/2005 |
| JP | 2006-230403 | | 9/2006 |
| WO | WO 2004/009827 | A | 1/2004 |
| WO | WO 2005/083101 | A1 | 9/2005 |
| WO | WO 2007/091731 | A | 8/2007 |

OTHER PUBLICATIONS

Yokochi et al., Applied Microbiology and Biotechnology, 1998.*
Kumon et al., Applied Microbiology and Biotechnology, 2002.*
Peberdy et al., Microbios, 1975.*
Yaguchi et al, JAOCS, vol. 74, No. 11, 1997, pp. 1431-1434.*
Preveen et al., Biotechnology Letters, 2006, vol. 28: pp. 197-202.*
Taichi Goya et al., "Research of New High-Degree Unsaturated Fatty Acid Producing . . . ", Abstracts of Lectures at 36th Meeting in Oil Chemistry, 1997, p. 160 (2E13).
Masashi Sakai et al., "Phosphatidylserine and Brain Function", Oil Science, 2002, pp. 23-28, vol. 2, No. 2, Japan.
Osman Kafrawy et al., "Docosahexaenoic acid in phosphatidylcholine mediates cytotocitity more effectively . . . ", Cancer Letters, 1998, pp. 23-29, vol. 132 (1-2), U.S.
"In vivo conversion of triacylglycerol to . . . " written by Hidetoshi Okuyama et al. in Biotechinology letters in Biotechinology letters, of Jul. 28, 2007, vol. 29, p. 1977-1981.
XP002577622, Database WPI, Week 200663 by Thomson in Scientific in GB p. 1-3 re JP-AP 20060022187 (Laid-Open No. 2006-230403) re new microorganism of labyrinthula group . . . .
XP002577624, Database WPI, Week 200226 by Thomson Scientific in GB p. 1-2 re JP-AP 20000133976 (Laid-Open No. 2001-309779) re method for producing highly unsaturated fatty . . . .
XP002577625, Database WPI, Week 200433 by Thomson Scientific in GB p. 1-2 re JP-AP No. 20020285886 (Laid-Open No. 2004-121019) re method for producing highly unsaturated . . . .

* cited by examiner

*Primary Examiner* — Allison Ford
*Assistant Examiner* — Yvonne Pyla
(74) *Attorney, Agent, or Firm* — RatnerPrestia

(57) ABSTRACT

Disclosed is a method for producing a DHA phospholipid comprising an ω3 unsaturated fatty acid, particularly DHA, as a constituent lipid by using a microorganism in a simpler manner. Specifically disclosed is a method for producing a phospholipid comprising an ω3 unsaturated fatty acid as a constituent lipid, which comprises the steps of: growing a microorganism capable of producing the ω3 unsaturated fatty acid in a culture medium containing a carbon source; and further culturing the grown microorganism in a culture medium without any carbon source. The method enables to produce a highly value-added phospholipid which comprises an ω3 unsaturated fatty acid as a constituent lipid by using a microorganism capable of producing the ω3 unsaturated fatty acid in a large quantity.

15 Claims, 3 Drawing Sheets

METHOD FOR PRODUCTION OF DHA-CONTAINING PHOSPHOLIPID THROUGH MICROBIAL FERMENTATION

TECHNICAL FIELD

The present invention relates to a method for producing a highly value-added phospholipid, and more specifically to a method for producing a phospholipid comprising an ω3 unsaturated fatty acid, particularly docosahexaenoic acid (DHA) as a constituent lipid, using a microorganism capable of producing the ω3 unsaturated fatty acid.

BACKGROUND ART

ω3 unsaturated fatty acids, such as eicosapentaenoic acid (EPA) and docosahexaenoic acid (DHA) in particular, are known as a functional lipid having physiological effects such as blood lipid reduction and improvement in brain and visual functions. Both EPA and DHA nutrients, which are essential to humans, can be insufficiently provided from foods taken. In order to ensure required dietary intake, health food materials containing EPA and DHA or dietary supplements are widely available. High-purity EPA ethyl ester is used in the form of a medicine such as a hypolipidemic agent. Since health foods containing EPA and DHA ingredients were approved as Foods for Specified Health Use by the Ministry of Health, Labour and Welfare in 2004, the market of ω3 unsaturated fatty acids such as EPA and DHA has been expected to grow, resulting in more widespread commercial use.

Meanwhile, in many cases, it has been reported that a phospholipids containing a fatty acid as a constituent lipid, rather than a fatty acids in itself, includes various useful bioactivities, such as improvement effect of brain function by phosphatidyl serine (PS) (Non-Patent Document 1) and improvement effects of arteriosclerosis and neurological dysfunction by phosphatidyl choline (PC). Recently, not only PS and PC, but also most phospholipids containing phosphatidyl ethanolamine (PE) have received much academic attention to be used in health care dietary supplements.

Under the circumstances, physiological functions such as antitumor and antioxidative properties of a phospholipid comprising an ω3 unsaturated fatty acid as a constituent lipid, for example, PC or PE comprising DHA as a constituent lipid (hereinafter called DHA-PC or DHA-PE, respectively, and most phospholipids containing DHA as a constituent lipid called DHA phospholipids) are being found in not only cases where a cultured cell is used, but also cases where an animal living body is used.

For example, according to a research by Kafrawy, et al. (Non-Patent Document 2), selective cytotoxicity to cancerated animal cells (mouse leukemia cells) is found in DHA-PC, particularly in a molecular species of PC comprising two molecules of DHA (DHAJDHA-PC). Thus, the demand for a phospholipid comprising an ω3 unsaturated fatty acid, particularly DHA, as a constituent lipid, is expected to grow in the future.

DHA phospholipid, which is a major phospholipid comprising an ω3 unsaturated fatty acid as a constituent lipid, is supplied, e.g., mainly from a squid (particularly, skin of neon flying squid), fish oil or eggs from hens produced by providing such fish oil (Patent Document 1). The neon flying squid contains plenty of phospholipids, 50% of which is phosphatidyl choline (PC), whose constituent lipid is DHA (50%), thereby showing a high proportion of DHA phospholipids to the lipid.

However, industrial production of DHA phospholipids, in which marine products such as neon flying squid and fish oil are defined as a source of DHA phospholipids, involves the following problems: unstable DHA phospholipid supply due to variable fish catches, uneven product quality from seasonal and climate changes and unassured product safety due to marine contamination. Additional problems are lower product quality and value due to unpleasant fish odor specific to fish oil and higher costs for refining long-chain highly-unsaturated fatty acids of structural similarity contained in fish oil. In eggs from hens, phospholipid content is high at 30% of yolk lipids, but weight of the total lipids is low. DHA content in ethanolic extract of the yolk is merely about 12%.

A source of an ω3 unsaturated fatty acid other than the above fish oil and eggs from hens is a microorganism capable of producing the ω3 unsaturated fatty acid, particularly a microorganism capable of producing DHA. A method for producing DHA using a microorganism is put into practical use in the United States and such products as ingredients of DHA-containing lipids and high-DHA containing feed are provided into the market. Specifically, a technology for growing genus *Thraustochytrium* or genus *Schizochytrium* (Patent Document 2) and a technology for using an ω3 unsaturated fatty acid extracted from *Thraustochytriales* (Patent Document 3) are developed.

Currently in Japan, various technologies for using labyrinthulean microorganisms as a source of DHA are developed, specifically a technology for using strain S3-2 as a microorganism of genus *Labyrinthula* (Patent Documents 4 to 6), and strain SR21 as a microorganism of genus *Schizochytrium* and technology for using it (Patent Documents 7 to 9).

However, all DHAs produced using the above-mentioned microorganisms are a mere DHA as a constituent lipid of fat (triglyceride), neither a constituent lipid of a phospholipid nor a constituent DHA phospholipid.

The inventors isolated a new labyrinthulean microorganism strain 12B as a non-photosynthetic unicellular microorganism to find out its capability of producing a DHA phospholipid and made a patent application (Patent Document 10). Despite this finding, the microorganism can accumulate over 40% DHA of fatty acid of the total lipids, but DHA phospholipid content is merely 12 to 13% of the total lipid of the microorganism.

Most DHA phospholipids prepared from biological materials includes only one molecule of DHA in a phospholipid molecule. In fact, very few biological material-derived phospholipids, in which the content of DHA as a constituent lipid exceeds 50%, are reported. Therefore, improvement in DHA content in a phospholipid is an important issue to increase the value for pharmaceutical use in addition to functional food.

PRIOR ART DOCUMENTS

Patent Document

[Patent Document 1] Japanese Unexamined Patent Application Publication No. 59-39258

[Patent Document 2] Japanese Unexamined Patent Application Publication (Translation of PC Application) No. 8-202405

[Patent Document 3] Japanese Unexamined Patent Application Publication (Translation of PC Application) No. 8-509355

[Patent Document 4] Japanese Unexamined Patent Application Publication No. 2001-275656

[Patent Document 5] Japanese Unexamined Patent Application Publication No. 2004-298798

[Patent Document 6] Japanese Unexamined Patent Application Publication No. 2003-000292

[Patent Document 7] Japanese Unexamined Patent Application Publication No. 9-000284

[Patent Document 8] Japanese Unexamined Patent Application Publication No. 10-072590

[Patent Document 9] Japanese Unexamined Patent Application Publication No. 10-310556

[Patent Document 10] Japanese Unexamined Patent Application Publication No. 2006-230403

Non-Patent Document

[Non-Patent Document 1] Masashi Sakai et al., "Phosphatidyl Serine and Brain Function," Oleo Science, Vol. 2, Nr. 2, pp 23-28, 2002

[Non-Patent Document 2] Kafrawy O et al., Cancer Lett., Vol. 132 (1-2), pp 23-29, 1998

SUMMARY OF THE INVENTION

Problems to be Solved by the Invention

It is, therefore, one object of the present invention to provide a method for producing a DHA phospholipid comprising an ω3 unsaturated fatty acid, particularly DHA, as a constituent lipid, using a microorganism in a simpler manner, without using fish oil or eggs from hens as a raw material.

Means of Solving the Problems

The inventors found that DHA phospholipid content and DHA phospholipid volume produced can be increased in the total lipid, not only by culturing a microorganism capable of producing an ω3 unsaturated fatty acid such as labyrinthulean strain 12B in particular in a normal culture medium containing a carbon source, but also further culturing the grown microorganism in a culture medium without any carbon source to complete the following inventions.

(1) A method for producing a phospholipid comprising an ω3 unsaturated fatty acid as a constituent lipid, comprising the steps of:

growing a microorganism capable of producing the ω3 unsaturated fatty acid in a culture medium containing a carbon source; and further culturing said grown microorganism in a culture medium without any carbon source.

(2) The method for producing a phospholipid according to item (1), wherein a microorganism capable of producing an ω3 unsaturated fatty acid is a labyrinthulean microorganism or a thraustochytride microorganism.

(3) The method for producing a phospholipid according to item (2), wherein labyrinthulean microorganism is labyrinthulean strain 12B.

(4) The method for producing a phospholipid according to item (2), wherein labyrinthulean microorganism is selected from the group consisting of genus *Labyrinthula* microorganism, genus *Thraustochytrium* microorganism and genus *Schizochytrium* microorganism.

(5) The method for producing a phospholipid according to item (4), wherein labyrinthulean microorganism is a strain S3-2 of genus *Labyrinthula* or a strain SR21 of genus *Shizochytrium.*

(6) The method for producing a phospholipid according to any one of items (1) to (5), wherein an ω3 unsaturated fatty acid is docosahexaenoic acid.

(7) The method for producing a phospholipid according to any one of items (1) to (6), wherein a grown microorganism is cultured in a culture medium without any carbon source under forced aeration.

Advantageous Effect of the Invention

The present invention can produce a highly value-added phospholipid comprising an ω3 unsaturated fatty acid as a constituent lipid, using a microorganism capable of producing the ω3 unsaturated fatty acid in a large quantity.

BRIEF DESCRIPTION OF THE DRAWINGS

The above and other objects in this invention will be seen by reference to the description taken in connection with the drawings, in which.

BEST MODE FOR CARRYING OUT THE INVENTION

Figure 1:
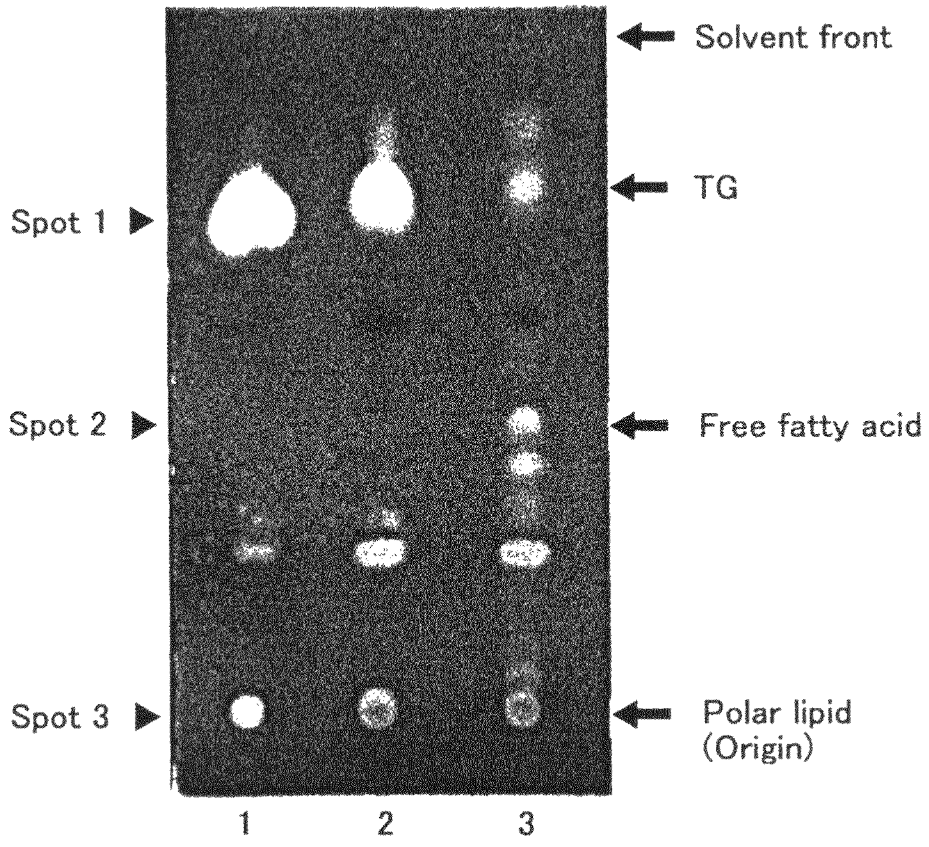
FIG. 1 shows a chromatogram of one-dimensional TLC of total lipids of labyrinthulean strain 12B cell cultured in F culture medium and Z1 culture medium. (Lane 1: total lipids (250 μg) in F culture medium 72 hours after culturing at 30° C., Lane 2: total lipids (250 μg) in Z1 culture medium 24 hours after culturing at 30° C., Lane 3: total lipids (250 μg) in Z1 culture medium 48 hours after culturing at 30° C.

An ω3 unsaturated fatty acid in this invention may be linolenic acid, octadecatetraenoic acid, eicosatetraenoic acid, EPA or DHA, but preferably EPA or DHA, and more preferably DHA.

A microorganism capable of producing an ω3 unsaturated fatty acid may be genus *Mortierella* microorganism such as *Mortierella alpina*, genus *Desmarestia* microorganism such as *Desmarestia acculeata*, dinoflagellates such as *Crypthecodinium cohnii*, labyrinthulean microorganism, etc. A labyrinthulean microorganism belongs to specifically *Labyrinthulaceae* consisting of genus *Labyrinthula* such as genus *Labyrinthula* strain S3-2 (accession number: FERM BP-7090), and *Thraustochytriaceae* consisting of genus *Labyrinthuloides*, genus *Corallochytrium*, genus *Aplanochytrium*, genus *Althornia*, genus *Japonochytrium*, genus *Ulkenia*, genus *Thraustochytrium* and genus *Schizochytrium* such as *Schizochytrium* strain SR21 provided with acceptance number FERM BP-5034.

Also, a microorganism capable of producing an ω3 unsaturated fatty acid may be labyrinthulean strain 12B as labyrinthulean microorganism, which was isolated by the inventors and deposited at the National Institute of Technology and Evaluation (NITE), Patent Microorganisms Depository (NPMD, Location: 2-49-10 Nishihara, Shibuya-ku, Tokyo, 151-0066 Japan) on Jan. 24, 2005, and provided with acceptance number NITE P-68. A particularly preferable microorganism in a method for producing a phospholipid in this invention is the labyrinthulean strain 12B. The detailed properties thereof are described in a Patent Document (Japanese Unexamined Patent Application Publication No. 2006-230403).

A method for producing a phospholipid comprises culturing a microorganism capable of producing an ω3 unsaturated fatty acid in a culture medium containing a carbon source. In this process, the microorganism is not cultured under specific conditions, but under normal conditions using a culture medium containing sugar and other carbon sources, in which the microorganism capable of producing the ω3 unsaturated fatty acid used can grow its number of cells and accumulate triglyceride, fatty acids, phospholipid and other lipids in a microbial cell body. Therefore, according to culture conditions for each microorganism used to favorably grow, such as temperature, culture medium composition, culture medium pH, oxygen concentration, intensity of light, shaking rate and cultivation time, a culture medium containing a carbon source suitable for growing the microorganism may be selected accordingly.

A culture medium may be a PY culture medium (1 g of polypeptone and 0.5 g of yeast extract per 1 L of artificial seawater having approximately 50% salt concentration, Kumon et al., Appl. Microbiol. Biotechnol., Vol. 60, pp 275-280, 2002) for Labyrinthulaceae microorganism, a seawater culture medium (yeast extract—peptone—glucose, 10 g, 10 g and 80 g, respectively per 1 L of water, 500 mL) for Thraustochytriaceae microorganism and a seawater salt culture medium (yeast extract—peptone—glucose, 2 g, 9 g and 25 g, respectively per 1 L of water) for dinoflagellates. A culture medium may be liquid, solid or semi-solid having shape maintaining property. In the above culturing process, when a culture medium is solid, lower limits of moisture content added to the culture medium are preferably 45% (v/w) or more, and upper limits of moisture content are preferably 60% (v/w) or less, more preferably 45 to 50%.

A carbon source can be added to the above culture medium beforehand and/or upon culturing. The volume of a carbon source may be sufficient if cells of the microorganism used increase as cultivation time is elapsed to accumulate triglyceride, fatty acids, phospholipid and other fat in a microbial cell body. In the above culturing process, static culture or shaking culture can be selected accordingly.

A method for producing a phospholipid in this invention comprises further culturing the microorganism grown by the above process in a culture medium without any carbon source. This method is not limited to the following assumptions, but by favorably growing a microorganism capable of producing an ω3 unsaturated fatty acid which stores plenty of triglyceride containing the ω3 unsaturated fatty acid in a microbial cell body in a culture medium containing a carbon source and further culturing the microorganism in a culture medium without any carbon source, bioconversion of the triglyceride stored in the microbial cell body into a phospholipid comprising the ω3 unsaturated fatty acid as a constituent lipid can increase content of phospholipid comprising the ω3 unsaturated fatty acid as a constituent lipid in the total phospholipid and then phospholipid volume produced comprising the ω3 unsaturated fatty acid as a constituent lipid.

"Culture medium without any carbon source" in this invention means a culture medium containing no carbon sources such as rice bran, wheat bran, acetic acid and ethanol, as well as sugar such as glucose and starch in particular, which are preferentially used by the microorganism in this invention, rather than triglyceride accumulated in a microbial cell body. Also, "culture medium without any carbon source" in this invention means a culture medium containing a small amount of a carbon source if the microorganism can grow using fat accumulated in a microbial cell body and produce a phospholipid comprising an ω3 unsaturated fatty acid as a constituent lipid, for example, a culture medium containing a carbon source cultivated in advance when a microorganism grown by a "culture medium containing carbon source" is collected and directly used, or a culture medium containing a small amount of carbon source partially found in peptone and other compositions composed of the culture medium.

In addition, "culture medium without any carbon source" in this invention is preferably a culture medium containing nutrients required or preferable for the microorganism to grow. Such a culture medium, culture conditions and examples thereof may be identical to those of said "culture medium containing carbon source," and culture conditions for accumulating fat in a microbial cell body by culturing the microorganism using the "culture medium containing carbon source." Other ingredients and compositions composed of the culture medium, other than the carbon source, may be selected for a microorganism used to favorably grow.

A particularly preferable embodiment in this invention is a method for producing DHA phospholipid, using labyrinthulean strain 12B as a microorganism. When the labyrinthulean strain 12B is cultured in a culture medium containing glucose as a carbon source at 30° C., it accumulates about 15 g/L lipid (as fatty acids) in a cell. Thus, the labyrinthulean strain 12B is advantageous in abundantly containing fat (triglyceride; TG) useful as a carbon source when the microorganism is grown in a culture medium without any carbon source. Additionally, the labyrinthulean strain 12B is a preferable microorganism due to DHA as 40% or more of fatty acids accumulated in labyrinthulean strain 12B grown by the culture medium containing a carbon source and conversion into DHA phospholipid using the DHA.

The labyrinthulean strain 12B is a preferable microorganism in this invention due to its favorable growth in a culture medium having relatively simple compositions, for example, a culture medium containing 50% seawater, 1% peptone, 1% yeast extract and 8% glucose (hereinafter called F culture medium) and reduction in production costs.

In a method for producing a DHA phospholipid using labyrinthulean strain 12B, the above F culture medium can be used as a preferable example of "culture medium containing carbon source." As a "culture medium without any carbon source," a culture medium, in which glucose is removed from the above F culture and other ingredients useful as a carbon source such as rice bran are not used (hereinafter called Z1 culture medium), can be used as a preferable example.

A method for producing a DHA phospholipid using labyrinthulean strain 12B is to inoculate labyrinthulean strain 12B cell into a proper amount of F culture medium, perform shaking culture at 30° C. for 24 to 72 hours and grow labyrinthulean strain 12B. Afterward, by adding part of the culture solution or cells collected by centrifugal separation from the culture solution to a proper amount of Z1 culture medium, further culturing of the microorganism at 30° C. for 24 to 72 hours can be exemplified. This method can contain more DHA phospholipids in cells of labyrinthulean st rain 12B than a case, in which culturing in F culture medium is completed. In the "culture medium without any carbon source," the culturing of the microorganism is more preferably under forced aeration.

A method for producing a DHA phospholipid in this invention may comprise the steps of extracting or collecting a phospholipid comprising an ω3 unsaturated fatty acid obtained by the above process as a constituent lipid from a microbial cell body, and refining the phospholipid as required. Collection and refinement of a phospholipid accumulated in a microorganism's cell body can be performed, for example, according to a method described in Bligh et al. (Can. J. Biochem. Physiol., Vol. 37, pp 911-917, 1959).

Also, a phospholipid comprising an ω3 unsaturated fatty acid produced by this invention as a constituent lipid can be directly used for food, food additive, feed additive, pharmaceuticals, etc., and may be added to food, dietary supplements, feed, pharmaceuticals or ingredients thereof.

EXAMPLE

This invention is described in more detail with reference to Examples. This invention is not limited to the Examples, and those skilled in the art can change, correct and modify the Examples within the scopes of this invention. In the following Examples, weight % is simply denoted as "%."

Example 1

1 platinum loop (approximately 1 mg) of labyrinthulean strain 12B cells preserved in an agar plate culture medium containing $By^+$ culture medium (0.1% peptone, 0.1% yeast extract, 0.5% glucose, 50% seawater and 1.0% agar) was inoculated into 10 mL of F culture medium (50% seawater, 1% peptone, 1% yeast extract and 8% glucose), and cultured at 30° C. for 72 hours. The turbidity of culture solution after culturing ($OD_{600}$) was about 36. 4 mL of the culture solution was inoculated into 25 mL of Z1 culture medium (culture medium in which glucose is removed from F culture medium) and cultured at 30° C. for 48 hours. During the culturing, $OD_{600}$ of the culture solution was measured as time was elapsed, and dry cell weight after culturing, weight of total lipids extracted from dry cells, TG volume in the total lipids, phosphorus volume, proportion of phospholipid weight calculated from the phosphorus volume to the total lipids, and DHA content in fatty acids from the total lipids were calculated (see Table 1).

1 platinum loop of labyrinthulean strain 12B cells is equivalent to about 0.5 mg of microbial cell body in dry weight. The microbial cell body was inoculated into 10 mL of F culture medium and cultured for 72 hours. Then, the dry weight of the microbial cell body was 246 mg by calculating from OD value. Meanwhile, 1 platinum loop of labyrinthulean strain 12B cells was directly inoculated into 10 mL of Z1 culture medium and cultured at 30° C. for 72 hours. The dry cell weight calculated from OD value after culturing was 16.3 mg, which was 7% of that cultured in F culture medium. It is thus believed that a property of growth of labyrinthulean strain 12B of direct culturing using Z1 culture medium is significantly low.

On the other hand, the dry weight (corresponding value) of labyrinthulean strain 12B cells contained in 4 mL of a culture medium which was cultured for 72 hours in F culture medium was 90.6 mg. The dry weight (corresponding value) of labyrinthulean strain 12B cells obtained by culturing the microorganism in Z1 culture medium, into which the labyrinthulean strain 12B cells were inoculated for 48 hours, was 235 mg, showing a 2.6-fold increase. In 48-hour culturing using Z1 culture medium, the weight of total lipids extracted from the cells declined from 38.8 mg to 22.0 mg by approximately 43% decrease, and TG (as volume of fatty acids) in the total lipids showed a significant decrease from 66.8% to 5.4%.

From these results, it is suggested that endogenous lipids accumulated in labyrinthulean strain 12B cells by culturing the microorganism in Z1 culture medium without any carbon source, particularly TGs, were consumed for growth of labyrinthulean strain 12B.

Meanwhile, phospholipid content (corresponding value from phosphorus volume) in total cellular lipids of labyrinthulean strain 12B cells 48 hours after culturing in Z1 culture medium showed about 3-fold increase, from 5.0 mg to 14.8 mg, and phospholipid content in the total lipids increased about 5 times from 12.9% to 67.3%. DHA content in the total lipids was 44.7% in cells cultured in F culture medium, and increased in cells cultured in Z1 culture medium according to cultivation time, about 57% 48 hours after culturing, indicating increase in DHA content comprising a phospholipid as a constituent lipid in labyrinthulean strain 12B cells.

Example 2

Like in Example 1, 4 mL of culture solution of F culture medium, in which labyrinthulean strain 12B cells were cultured, was inoculated into 25 ml of Z2 culture medium containing 2% peptone and 2% yeast extract, and 25 mL of Z4 culture medium containing 4% peptone and 4% yeast extract, and cultured at 30° C. for 48 hours. The turbidity after culturing, dry weight of collected cells, weight of total lipids extracted from dry cells, phosphorus volume in the total lipids, phospholipid weight calculated from the phosphorus volume, their proportions and DHA content were determined (see Table 1). The phospholipids were quantified by measuring inorganic phosphorus volume using phosphatidyl serine (Sigma) as a standard preparation.

Consequently, by increasing the contents of peptone and yeast extract, the yield of labyrinthulean strain 12B cells rises (235 mg in Z1 culture medium, 243 mg in Z2 culture medium and 339 mg in Z4 culture medium). In Z4 culture medium, a cell yield was about 4 times that of microorganism inoculation (dry cell weight of 90.6 mg in 4 mL of culture solution cultured in F culture medium). The weight of the total lipids collected from cells after culturing was completed were 28.5 mg and 40.0 mg in Z2 culture medium and Z4 culture medium, respectively.

The phospholipid contents in total cellular lipids of labyrinthulean strain 12B cultured in Z2 culture medium and Z4 culture medium were 14.9 mg and 20.8 mg, respectively, both of which were higher than 14.8 mg in cases where it was cultured in Z1 culture medium. However, the proportions were 52.3% and 52.0% in Z2 culture medium and Z4 culture medium, respectively and lower than 67.3% in Z1 culture medium. Also, TG proportion in the total lipids increased as the concentrations of peptone and yeast extract in Z culture medium increased.

The increase in the concentration of peptone and yeast extract in Z culture media declined the ratio of phospholipid to total lipids, and it was confirmed that increase in volume of cells grown can raise phospholipid volume produced.

Example 3

Culture mediums, in which 1 mM $K_2PO_4$, 1 mM $K_2PO_4$+1 mM serine, 1 mM $K_2PO_4$+1 mM ethanolamine were added to Z1 culture medium (hereinafter called Z1p, Z1ps and Z1pa), were prepared. By culturing like in Example 1, the turbidity after culturing, dry cell weight of cells collected, weight of total lipids extracted from dry cells, phosphorus volume in the total lipids, phospholipid weight calculated from phosphorus volume, their proportions and DHA content were determined.

As a result, phospholipid weight was increased in Z1ps (15.2 mg). From the results, it was confirmed that by adding inorganic phosphorus and amino acid to each culture medium, volume of phospholipid produced can be increased.

Table 1 shows analytical results of the above Example 1 to 3.

lecting 30 mL of culture solution, and by determining dry cell weight, weight of total lipids, total phospholipid weight, the data per total culture solution was obtained. DHA content was calculated by GC after methanolysis of total lipids. The con-

TABLE 1

Effects of medium composition and cultivation time on cell growth, phospholipid content and DHA content of labyrinthulean strain 12B

| | Medium | | | | | | | | |
|---|---|---|---|---|---|---|---|---|---|
| | F | Z1 | Z1 | Z1 | Z2 | Z4 | Z1 | Z1 | Z1 |
| Glucose | +[a] | −[a] | − | − | − | − | − | − | − |
| $K_2HPO_4$ | − | − | − | − | − | − | + | + | + |
| Ethanolamine | | | | | | | − | + | − |
| Serine | − | − | − | − | − | − | − | − | + |
| Cultivation time (h) | 72 | 8 | 24 | 48 | 48 | 48 | 48 | 48 | 48 |
| Turbidity of culture solution (600 nm) Start of culturing/End of culturing | 0.2[b]/36.7 | 4.87/27.2[c] | 5.20/21.7[c] | 4.9/22.0[c] | 4.8/19.3[c] | 5.0/22.6[c] | 5.4/22.7[c] | 4.81/19.5[c] | 4.75/23.0[c] |
| Dry cell weight in F media after culturing is completed (mg/4 mL) | 90.6 | | | | | | | | |
| Dry cell weight in Z media after culturing is completed (mg/29 mL) | | 140 | 249 | 235 | 243 | 339 | 205 | 172 | 233 |
| Cell density (mg/mL) | 22.7 | 4.8 | 8.6 | 8.1 | 8.4 | 11.7 | 7.1 | 5.9 | 8.0 |
| Total lipid weight derived from dry microbial cell body (mg) | 38.8 | 32.0 | 39.7 | 22.0 | 28.5 | 40.0 | 22.2 | 18.6 | 25.5 |
| TG derived from total lipid (mg)[d] | 25.9 | ND[e] | 12.5 | 1.2 | 6.2 | 13.9 | ND[e] | ND[e] | ND[e] |
| TG/total lipid (%) | 66.8 | ND[e] | 48.6 | 5.4 | 21.8 | 34.8 | ND[e] | ND[e] | ND[e] |
| Phospholipid derived from total lipid (mg)[f] | 5.0 | 8.7 | 11.3 | 14.8 | 14.9 | 20.8 | 10.5 | 11.1 | 15.2 |
| Phospholipid/total lipid (%) | 12.9 | 27.2 | 28.5 | 67.3 | 52.3 | 52.0 | 47.3 | 59.7 | 59.6 |
| Phospholipid/dry cell weight (%) | 5.5 | 6.2 | 4.5 | 6.3 | 6.1 | 6.1 | 6.5 | 6.5 | 6.5 |
| DHA/total fatty acid (%) | 44.7 | 47.2 | 53.3 | 56.5 | 55.3 | 55.4 | ND | ND | ND |

[a] +; contained, −; not contained
[b] $OD_{600}$ value when cells collected using a platinum loop were suspended into 10 mL of F medium.
[c] Correct $OD_{600}$ values cannnot be obtained due to aggregation of some cells, approximate values are shown.
[d] By one-dimensional development of total lipids by TLC, TG spots were subjected to methanolysis. TG volume was quantified as volume of fatty acids.
[e] ND; not determined
[f] Phosphorus volume in total lipids quantified is converted into phospholipid weight.

Example 4

1) 1 platinum loop of cells of labyrinthulean strain 12B preserved on an agar plate of By culture medium was inoculated into 200 mL of F culture medium in 500 mL flask and cultured in advance at 30° C. for 3 days. 100 mL of the solution cultured in advance was added to 625 mL of Z1 culture medium/2.5 L jar fermentor (JF: Tokyo Rikakikai Co., LTD), aerated to JF head space (1000 mL/min) and cultured at 30° C. for 24 hours at an agitation rate of 300 rpm. Under the culture conditions, loss from foaming of culture solution can be reduced without using a defoaming agent. After col- tainer is flask and cultivation time was 48 hours without aeration under the above culture conditions. As a control, flask culture was performed.

Under the above culture conditions, cell concentration of culture solution after culturing was 5.7 mg/mL, and phospholipid weight per hour was 565 μg/mL/24 hours. This value was about twice that of the control (flask culture: 225 m/mL/24 hours).

2) Culturing was performed with a JF agitation rate of 500 rpm under the above conditions in 1). The cell concentration of a culture solution after culturing was 6.9 mg/mL, and the phospholipid weight per hour was 642 μg/mL/24 hours.

3) Cell were cultured under the above conditions in 1), except for aeration in culture medium (110 mL/min) in addition to JF head space. The cell concentration of culture solution after culturing was 7.7 mg/mL, and the rate of generating phospholipid weight increased to 755 μg/mL/24 hours (about 3 times that of control flask culture).

Table 2 shows the results of the above 1), 2) and 3).

TABLE 2

| | Control | JF Culture 1) | JF Culture 2) | JF Culture 3) |
|---|---|---|---|---|
| Cell concentration (mg/mL) | 8.1 | 5.7 | 6.9 | 7.7 |
| Total lipid/cell weight (%) | 9.3 | 12.8 | 16.2 | 17.6 |
| Total phospholipid/total lipid (%) | 67.3 | 77.8 | 57.2 | 66.9 |
| Total phospholipid/cell weight (%) | 6.3 | 10 | 9.3 | 11.5 |
| Total phospholipid (μg/mL culture solution/24 hours) | 225 | 565 | 642 | 755 |
| DHA volume per total fatty acid | 56 | 52 | 45 | 49 |

<Method of Analysis>

Each analysis regarding the above Examples was performed as follows.

1) Extraction of Total Lipids

The lipids extracted from a dry microbial cell body by a conventional method (Non-Patent Document 11) using chloroform methanol were defined as total lipids. In order to separate polar lipid from the total lipids, 100 μg of sample of the total lipids was subjected to one-dimensional thin-layer chromatography (TLC) using silica gel plate (MERCK, silica gel G60). The composition of a developing solvent was hexane-ether-acetic acid (50:50:1, volume percent). After development, primulin was sprayed on a plate to confirm the location of spots under UV irradiation. TG was identified by comparing its $R_f$ with that of its authentic standard.

2) Identification of Phospholipid

The total lipids (1 mg) were subjected to two-dimensional TLC. TLC plates were developed with a mixture of chloroform, methanol, and water (65:25:4, by volume; solvent A) for the first development and with a mixture of chloroform, acetone, methanol, acetic acid, and water (50:20:10:10:1, by volume; solvent B) for the second development, and a reagent specific to polar radical was sprayed thereon. A subject spot was scraped off the plate and phospholipids were extracted with chloroform/methanol mixed solution. The phospholipids were identified according to reactivity against detection reagents on a TLC plate and comparison of $R_f$ by one-dimensional TLC using 3 different types of developing solvents A, B, and C. Solvent C composed of chloroform, methanol, and ammonia water (50:20:10, by volume)).

After culturing in F culture medium at 30° C. for 72 hours, and culturing in Z1 culture medium at 30° C. for 48 hours, the results of one-dimensional TLC of total lipids extracted from labyrinthulean strain 12B are shown in FIG. 1. Spot 1 is TG and spot 2 is free fatty acid. The origin (spot 3) is polar lipid. Table 2 shows proportions based on TG, free fatty acid, polar lipid, and fatty acid volume of other neutral lipid.

TABLE 3

Lipid composition and DHA content of labyrinthulean strain 12B cultured in F culture media and Z culture media

| Medium | Proportion in total lipids[a], % (DHA ratio, %) F | Z × 1 | Z × 2 | Z × 4 |
|---|---|---|---|---|
| TG | 88.4 (40.8) | 12.7 (52.6) | 34.7 (58.8) | 38.8 (42.5) |
| Free fatty acid | 0[b] | 9.3 (28.8) | 12.6 (29.7) | 5.5 (40.6) |
| Polar lipid[c] | 8.1 (56.4) | 72.6 (56.6) | 47.4 (57.1) | 50.5 (51.5) |
| Other lipids | 3.5 (32.7) | 5.4 (31.7) | 5.4 (29.3) | 5.2 (36.9) |

[a]Total lipids are separated by one-dimensional thin-layer chromatography and respective lipid class volumes are expressed as relative fatty acid volume.
[b]Not detected
[c]Lipid which didn't move from the origin by thin-layer chromatography is defined as polar lipid.

Transfer of labyrinthulean microorganism strain 12B cells from F culture medium to Z culture medium declines TG, and increases proportions of free fatty acids and polar lipid. Culturing in Z2 culture medium and Z4 culture medium also showed decline in TG and increase in polar lipid like culturing in Z1 culture medium, but not so significant as in Z1 culture medium. DHA content of polar lipid exceeded TG DHA content, other than those of cells cultured in Z2 culture medium.

Figure 2A:
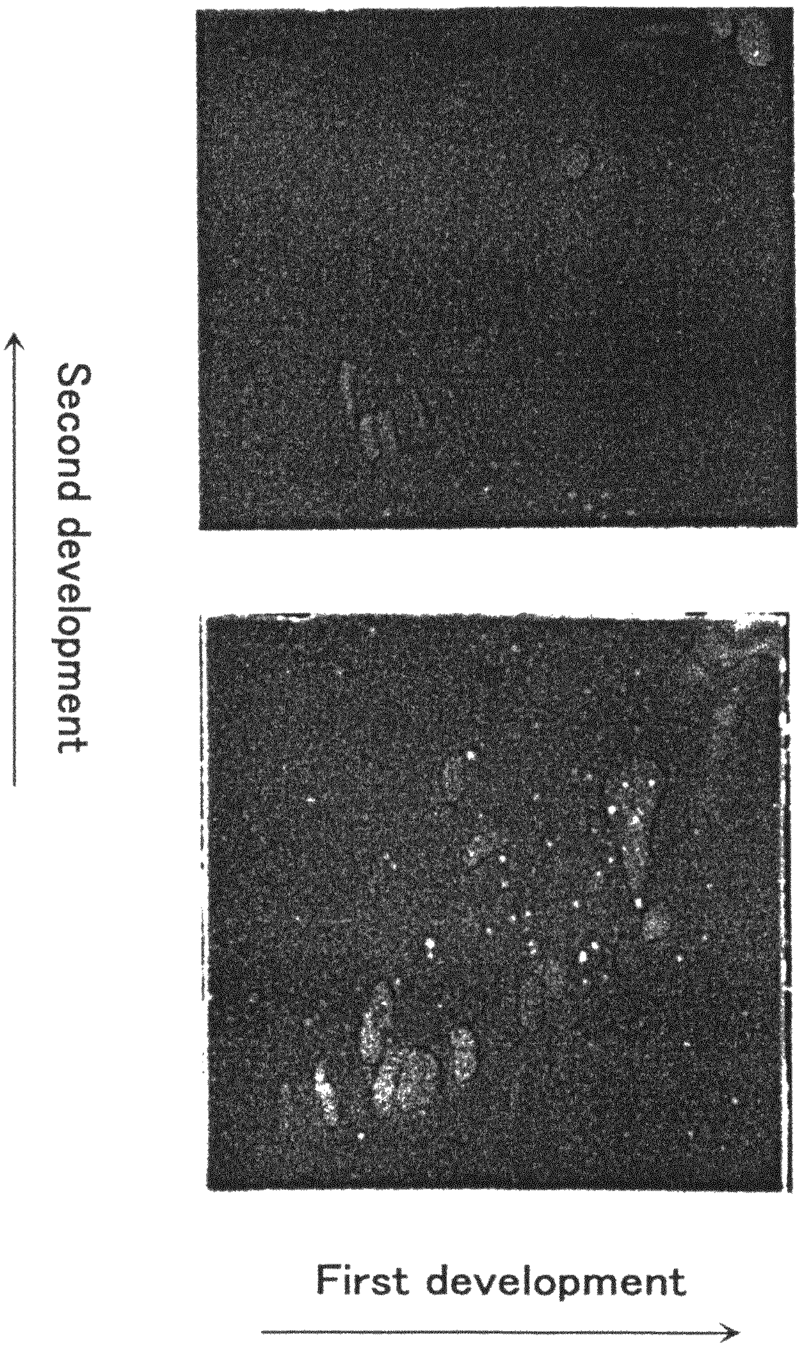
FIG. 2*a* shows a chromatogram of two-dimensional TLC of total lipids of labyrinthulean strain 12B cell cultured in F culture medium and Z1 culture medium (photographed under UV irradiation after spraying with primulin). (Upper panel: total lipids (1 mg) in F culture medium 72 hours after culturing at 30° C., lower panel: Z1 total lipids (1 mg) in culture medium 48 hours after culturing at 30° C.)
Figure 2B:
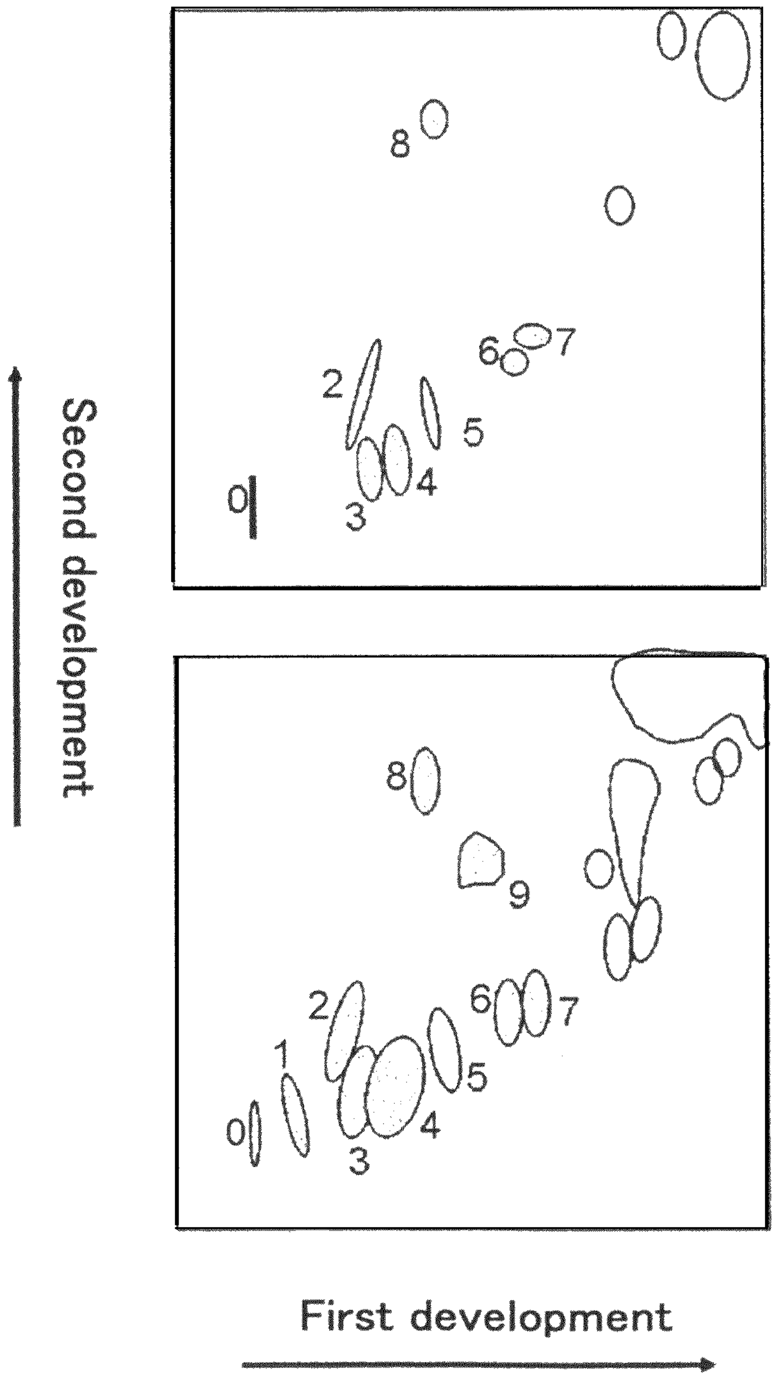
FIG. 2*b* schematically shows the chromatogram as shown in FIG. 2*a*. (Spots 1 to 9 denote a phospholipid. (Upper panel: total lipids in F culture medium 72 hours after culturing at 30° C., lower panel: total lipids in Z1 culture medium 48 hours after culturing at 30° C.).

FIG. 2 shows the results of two-dimensional TLC of total lipids. FIG. 2*a* is a photo taken under ultraviolet irradiation after spraying fluorescent substance (primulin) on a plate, and FIG. 2*b* schematically shows FIG. 2*a*. Each spot is numbered as shown in FIG. 2*b*. The reactivity against a detection reagent of lipid giving each spot was examined. Lipids 1, 2, 3, 4, 6, 7, 8 and 9 are positive to Dittmer reagent, all indicating phospholipids. From the reactivity of these lipids against other detection reagents, lipid 2 was identified as phosphatidylinositol (PI), lipids 3 and 4 as phosphatidyl choline (PC1 and PC2), and lipids 6 and 7 as phosphatidyl ethanolamine (PE1 and PE2). The results were confirmed by comparing $R_f$ with those of respective authentic standards. Due to 2 spots provided by both PC and PE, it is suggested that constituent fatty acids (particularly, DHA content) are different. Other polar lipids containing phospholipids are not identified. 0 denotes the origin, and spot 5 and unnumbered spot are lipids which are negative to Dittmer reagent.

3) Phospholipid Composition and DHA Content

After culturing in Z1 culture medium at 30° C. for 48 hours, total lipids extracted from labyrinthulean strain 12B cell were subjected to two-dimensional TLC, and all spots of lipids derived from Z1 culture medium were scraped off and phosphorus was quantified according to a method by Istokovics et al. (Can. J. Microbiol., Vol. 44, pp 1051-1059, 1988). The volume percentage to total phospholipids was 61.3% in PC, 11.9% in PE, 12.5% in PI, and 14.6% in others. When the volume of fatty acids was employed in PC and PE, the percentage was 46.0% and 54.0% in PC1 and PC2, respectively, and 46.7% and 53.3% in PE1 and PE2, respectively.

In addition, the product was subjected to methanolysis according to a conventional method, together with heneicosanoic acid as an internal standards having a known amount (200 μg), and fatty acid methyl ester was analyzed by GC. In PC1 and PC2, 39.2% and 66.8% of total fatty acids were DHA, respectively, and in PE1 and PE2, 23.0% and 33.3% of total fatty acids were DHA, respectively. DHA content in PI was 20.9%. Thus, DHA was found to be a constituent lipid in PC, particularly in PC2. The DHA contents of total PC and total PE calculated were 54.0% and 28.4%, respectively. Table 3 shows the results. DHA content of phospholipids in Table 3 was lower than DHA content (56.5%) of total lipids derived from cells cultured in Z1 culture medium (see Table 1), DHA content (56.6%) of polar lipid, DHA content (52.6%) of TG, but this is attributed to decomposition of polyunsaturated fatty acids in the process of TLC or GC.

TABLE 4

Phospholipid composition, DHA content and yield of labyrinthulean strain 12B cultured in Z1 culture media for 48 hours

| | Proportion to total lipid[a] (%) | Proportion to total phospholipid[b] (%) | Proportion in each lipid class[c] (%) | DHA content (%) | Yield (mg/total culture solution (29 mL)) |
|---|---|---|---|---|---|
| Total phospholipids | 67.0 | | | | 14.8 |
| Total PC | | 61.0 | (100) | 54[e] | 10.8 |
| PC1 | | | 46.0 | 39.2 | 5.4 |
| PC2 | | | 54.0 | 66.8 | 5.4 |
| Total PE | | 11.9 | (100) | 28.4[f] | 2.0 |
| PE1 | | | 46.7 | 23.0 | 1.0 |
| PE2 | | | 53.3 | 33.3 | 1.0 |
| Total PI[d] | | 12.5 | | 20.9 | |
| Other phospholipids | | 14.6 | | | |

[a]Phosphorus volume in the total lipids measured is converted into phospholipid weight.
[b]By two-dimensional thin-layer chromatography, PC is incompletely separated into 2 subclasses of PC1 and PC2, and PE into 2 subclasses of PE1 and PE2. Subclasses are not differentiated when phosphorus volume is quantified.
[c]By differentiating PC end PE subclasses approximately, fatty acids are analyzed according to subclass. Proportion in quantity of PC1 and PC2 and PE1 end PE2 were calculated based on fatty acid volume.
[d]In PI, both phosphorus quantification and fatty acid analysis were performed as a single lipid class.
[e]DHA content was calculated based on DHA contents (%) in PC1 and PC2, and in PE1 and PE2.

The invention claimed is:

1. A method for increasing the content of a phospholipid comprising an ω3 unsaturated fatty acid as a constituent lipid in a microorganism capable of producing the ω3 unsaturated fatty acid, comprising the steps of:
   (a) growing the microorganism in a culture medium containing a carbon source, whereby the phospholipid is produced at a first level and stored in a microbial cell body of the microorganism; and
   (b) further growing the microorganism from step (a) in a culture medium without any carbon source, whereby the content of the phospholipid in the microorganism is increased to a second level that is greater than the first level.

2. The method as set forth in claim 1, wherein the microorganism is a labyrinthulean microorganism or thraustochytride microorganism.

3. The method as set forth in claim 2, wherein the labyrinthulean microorganism is labyrinthulean strain 12B.

4. The method as set forth in claim 2, wherein the labyrinthulean microorganism is selected from the group consisting of genus *Labyrinthula* microorganisms, genus *Thraustochytrium* microorganisms and genus *Schizochytrium* microorganisms.

5. The method as set forth in claim 1, wherein the ω3 unsaturated fatty acid is docosahexaenoic acid.

6. The method as set forth in claim 2, wherein the ω3 unsaturated fatty acid is docosahexaenoic acid.

7. The method as set forth in claim 3, wherein the ω3 unsaturated fatty acid is docosahexaenoic acid.

8. The method as set forth in claim 4, wherein the ω3 unsaturated fatty acid is docosahexaenoic acid.

9. The method as set forth in claim 1, wherein step (b) is carried out under forced aeration.

10. The method as set forth in claim 2, wherein step (b) is carried out under forced aeration.

11. The method as set forth in claim 3, wherein step (b) is carried out under forced aeration.

12. The method as set forth in claim 4, wherein step (b) is carried out under forced aeration.

13. The method as set forth in claim 5, wherein step (b) is carried out under forced aeration.

14. A method for increasing the content of a phospholipid comprising a docosahexaenoic acid as a constituent lipid in labyrinthulean strain 12B, comprising the steps of:
   (a) growing the labyrinthulean strain 12B in a culture medium containing a carbon source, whereby the phospholipid is produced at a first level and stored in a microbial cell body of the microorganism; and
   (b) further growing the labyrinthulean strain 12B from step (a) in a culture medium without any carbon source, whereby the content of the phospholipid in the microorganism is increased to a second level that is greater than the first level.

15. The method as set forth in claim 14, wherein the microorganism is grown under forced aeration.

* * * * *